United States Patent [19]

Dorr

[11] Patent Number: 4,944,186

[45] Date of Patent: Jul. 31, 1990

[54] ULTRASONIC MEASURING SYSTEM

[75] Inventor: John A. Dorr, Crofton, Md.

[73] Assignee: Xecutek Corporation, Annapolis, Md.

[21] Appl. No.: 277,604

[22] Filed: Nov. 29, 1988

[51] Int. Cl.$^5$ .............................................. G01N 29/00
[52] U.S. Cl. ......................................... 73/597; 73/644
[58] Field of Search ................................... 73/597, 644

[56] References Cited

U.S. PATENT DOCUMENTS 4,302,623 11/1981 Canfield ............................ 73/290 V
4,554,834 11/1985 Prinz et al. ............................. 73/644
4,594,897 6/1986 Bantz ..................................... 73/644

FOREIGN PATENT DOCUMENTS 88105168 7/1988 PCT Int'l Appl. .................... 73/644

Primary Examiner—Michael J. Tokar
Assistant Examiner—Mark A. Spector
Attorney, Agent, or Firm—Jim Zegeer

[57] ABSTRACT

Hot target ultrasonic measurement system in which an ultrasonic transducer for transmitting ultrasonic energy along a measuring path toward the hot steel ingot target receives a reflection echo of ultrasonic energy from the hot target along the measuring path, and electronic circuit for determining the range to the hot target from the time of transmission of said ultrasonic energy to the receipt of reflection of ultrasonic energy from said target. The temperature or speed of sound in the media in the measuring path is measured and used in the range measurement. A source of fluid measuring path media under pressure forms a column of fluid measuring path media is projected from the ultrasonic transducer to impinge on the hot target to enhance the accuracy of range measurements by minimizing the effect of temperature gradients due to the heat radiated from said hot target in said measuring path and narrow the distribution of reflection echo amplitudes, provide a more stable range of measurements and improve precision of range measurement by enhancing the accuracy of speed of sound in the media measurement.

15 Claims, 4 Drawing Sheets

WITHOUT AIR

WITH AIR COLUMN

ULTRASONIC MEASURING SYSTEM

BACKGROUND AND BRIEF DESCRIPTION OF THE INVENTION

Measurements of hot targets such as red or white hot ingots or slabs in a steel mill have always been difficult and in the case of ultrasonic measurements, the problem has been compounded by the fact that the hot slab is typically radiating tremendous heat creating a large number of temperature gradients in the air between the transducer and the target. Positioning one or more temperature sensors or other means utilized to determine the speed of sound in a given medium does not result in a good practical solution to the problem because of the wide differential in temperature in the measuring path air between the hot slab and the location at the ultrasonic transducer. Moreover, extreme temperatures of the hot target causes turbulent air flow around the target and this turbulent air flow also can cause variations in the time of travel of the ultrasonic energy to and from the hot ingot target.

I have discovered that by blowing air in the path between the transducer and the hot target, sharp temperature gradients are reduced and adverse effects of the temperature gradients on range measurement accuracy is greatly diminished or minimized. Moreover, the hot turbulent air flow in the measuring path is displaced to permit accurate measurement.

The object of this invention is to provide an improved ultrasonic measurement of hot targets by the elimination of temperature gradients and hot turbulent air flow into the measuring path between the ultrasonic transducer and the hot target such as a steel ingot. In a preferred embodiment, a fluid medium such as air under pressure is flowed from the transducer to the target to form a homogeneous column of air flowing towards and impinging upon the hot target to thereby establish an ultrasonic measuring path between the target and the ultrasonic transducer. This establishes an "artificial" measuring path between the ultrasonic transducer and the hot slab target in which the air is of substantially constant temperature and turbulent hot air flows at least in the measuring path area of the target is eliminated or minimized. Radiant heat from the target heats a thin layer of air but the high pressure jet of air from the target forms a measuring path column of air that is substantially homogeneous with respect to temperature and hence with respect to speed of ultrasonic energy in the medium. The air is caused to issue from a manifold which has one jet exiting into a plenum chamber containing the a temperature sensor and a plurality of jets circumferentially spaced around the transducer so as to provide as uniform and as turbulent-free a measuring path without the entrainment of too much ambient air into the measuring path.

Since the hot target may be radiating a large amount of thermal energy, the transducer itself is not in a direct line to the hot target but, rather, is positioned above a 45 degree reflector which has been painted with a black or an absorbent paint which prevents reflection of the radiant energy into the transducer. In a preferred embodiment, the transducer is a planar electrostatic transducer of the type sold by the Polaroid TM company but, in other embodiments can use more expensive transducers such as piezoelectric crystals including barium titanate and the like. The air flows into the plenum chamber is relatively cool and serves to cool the ultrasonic transducer, reflector and electronic circuitry therein.

Thus, the invention has the object of solving the problem of measuring any hot surface such as a red-hot slab such as a steel ingot in a mill. The column of air establishes a uniform homogeneous measuring path to within a very short distance of the target where the extreme heat of the target has significantly less effect on the measurement and can be better calibrated for accuracy. The transducer itself is contained within a plenum chamber and projects an narrow ultrasonic beam upon the 45 degree reflector so that the beam exists through an aperture or opening into a cowled chamber and the plurality of jet nozzles issue jets of high pressure air which merge into a homogenous column of air. For long range measurements (15-60 inches) at lower frequency, the jets are located outside the cowl and the cowl serves as a noise shield. For short range measurements at a higher frequency, the jet nozzles are located inside the cowled chamber and circumferentially spaced around the exit aperture adjacent the 45 degree reflector. The cowling itself may be a stainless-steel cylinder around or through which the column of air flows towards target and the target in space from 5 to about 45 inches from the end of the cowling. Separate regulator valve may be incorporated for adjusting the air flow interior of the plenum chamber and adjusting the air flowing through the circumferentially spaced jet nozzles. The housing may be insulated to protect the interior from heating excessively and creating temperature differentials in the portion of the measuring path MP which is located in the plenum chamber and hence temperature gradients which can adversely effect the measurement.

BRIEF DESCRIPTION OF THE DRAWINGS

The above and other objects, advantages and features of the invention will become more apparent when considered with the following specification and accompanying drawings wherein.

DETAILED DESCRIPTION OF THE INVENTION

Referring now collectively to FIGS. 1A-1F and 2A, 2B and 2C, a hot ingot HI which may be moving or stationary and typically in a steel mill, for example, may be red or white hot. As indicated in the diagram of FIG.

Figure 1A:
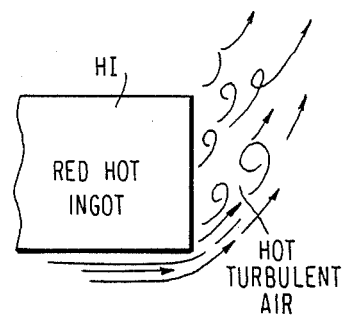
FIGS. 1A-1F are diagrammatic illustrations useful for achieving a better and full understanding of the invention.
Figure 1B:
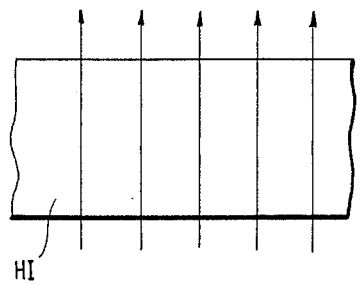
Figure 1C:
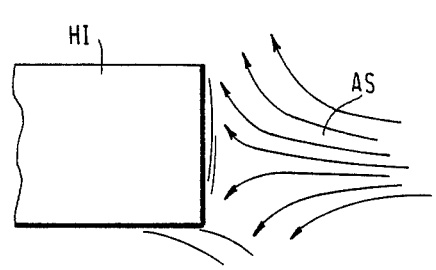
Figure 1D:
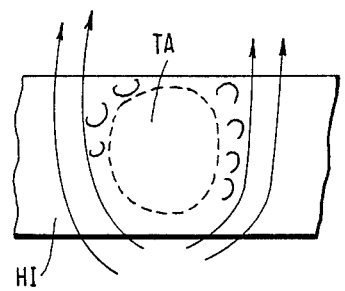
Figure 1E:
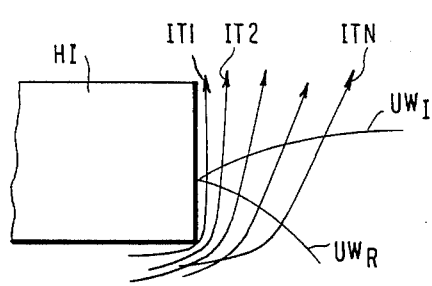
Figure 1F:
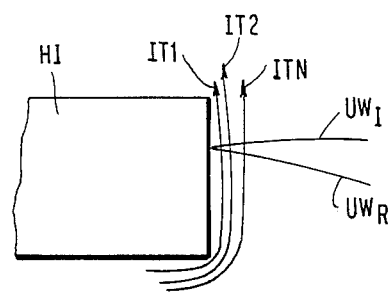

2B, and FIG. 1E, without air blowing on the hot ingot in the ultrasonic measuring area, the isotherms (contour lines of equal temperature) illustrate the air temperature falling off roughly according to the inverse square law with the temperature of the air nearest the target obviously being much hotter than the temperature at points more distant from the target.

FIG. 1A diagrammatically illustrates the flow of hot turbulent air from under and at the side of the hot ingot HI. The ingot typically is moving relatively slowly on a roller conveyor mechanism (not shown). The radiant energy from the hot ingot heats the surrounding air and the heated air tends to rise from below and creates turbulent air flow as indicated. These turbulences cause the ultrasonic echo to vary in strength, being stronger and weaker in an generally erratic fashion. An idealized flow pattern is diagrammatically illustrated in FIG. 1B.

According to the invention, an air stream AS, which, in the preferred embodiment of the invention, the air stream is substantially cooler than the air heated by the hot ingot, is blown or caused to flow and impinge upon the surface are of the hot ingot HI which is the target area TA (FIG. 1D) for making the ultrasonic range measurement. The air stream flow establishes a target area TA which is substantially free of hot turbulent air flow.

The temperature gradients diagrammatically illustrated by the isotherm lines IT1, IT2 . . . ITN (FIG. 1E and FIG. 2B) for non-turbulent flow cause a difraction or bending of the projected or inicident ultrasonic wave $UW_I$. (The ultrasonic wave paths shown in these sketches is exaggerated for purposes of illustration) and a complementary diffraction of the reflected ultrasonic wave $UW_R$ and this leads to error in the range measurement. However, when air is blown or impinges upon the hot ingot surface from the direction of ultrasonic, the transducer, diffraction of the ultrasonic waves $UW_I$ is significantly reduced leading to a substantial improvement in the accuracy of ultrasonic range measurements.

Figure 2A:
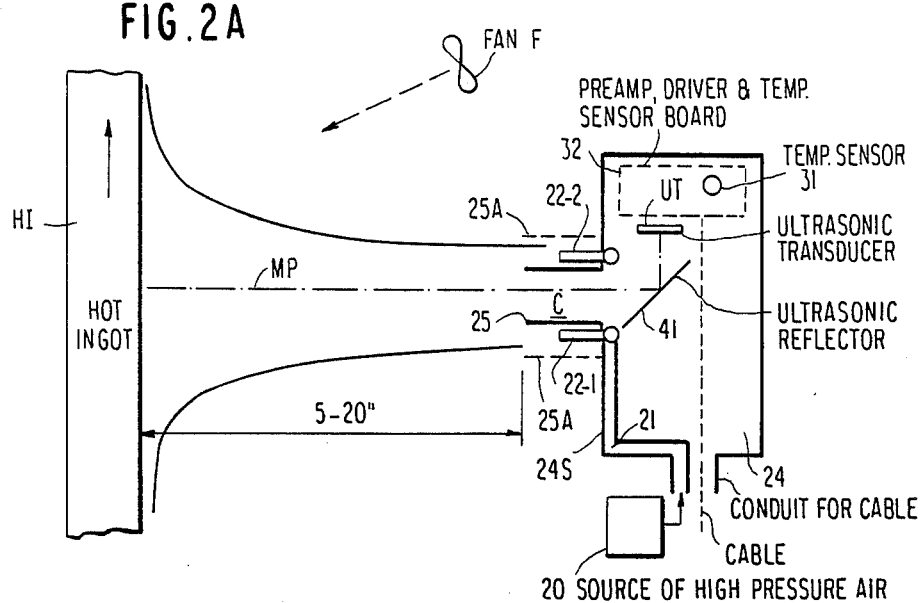
FIG. 2 is a side-sectional diagrammatic view of a ultrasonic ranging system incorporating the invention.
FIG. 2B illustrates the isotherms existing between the hot ingot target and the end of the cowling.
FIG. 2C illustrates the effect of the column of high pressure air in reducing the number of temperature gradients and providing a homogeneous column of air between a space closely adjacent to the surface of the target and the transducer cowling.

As shown in FIG. 2A, air under pressure is blown against the hot ingot HI from a source 20, is supplied to an air manifold 21 which has a plurality of jet nozzles 22—1, 22—2 . . . 22—N which are mounted on the exterior of the plenum chamber 24 and in the preferred embodiment the exteriorly of the chamber C formed by stainless-steel cowling 25 which is welded to the plenum chamber 24. The high pressure air exiting the jets can generate a noise and in this location, the cowling shields or isolates the transducer from such noise. The surfaces of the plenum chamber 24—S which are facing the hot ingot are well insulated so as to avoid and/or minimize the effect of the high radiant energy eminating from the hot ingot HI. In addition, a further jet nozzle 28 issues an interior air jet within the plenum chamber 24 and is connected to the air manifold 21 at the joint 27 and cools the transducer UT, reflector, and other. The air in the interior of the plenum chamber is controlled by a separate air control valve 29 and the air in the manifold is controlled by a valve 30 which controls the air issuing through the jet nozzles 22—1, 22—2 . . . 22—N. Thus, the pressure and flow rate of the air forming the column of air in the measuring path is essentially at the same temperature as the air within the plenum chamber 24. As indicated in FIG. 1A, the air in the plenum chamber is measured by a temperature sensor 31 which is mounted on a preamplifier and driver board 32 which are mounted within the plenum chamber 24.

Ultrasonic transducer UT is mounted on a bracket 40 which is secured to the insulated front side wall of the chamber 24 and faces in a downward direction when the plenum chamber is mounted on a support standard, or wall (not shown) adjacent the hot ingot's path. Ultrasonic reflector 41 is at an angle of about 45 degrees to the axis of the ultrasonic transducer UT and the axis of the measuring path MP which defines the axis of the main single central lobe (which is normally a conical) of the ultrasonic transducer which is a narrow beam when operated at a frequency of about 50 kHz. In general, transducer construction of the type utilized herein of the type sold by the Polaroid TM Corporation are well known in the art and an example may be found in Muggli U.S. Pat. Nos. 4,081,626 and 4,199,246 wherein a single transducer both transmits bursts of sonic energy towards a target and detects echoes of reflected sonic energy from the target for ranging purposes.

As noted above, and as well known in the art, when an ultrasonic energy pulse is transmitted through media of varying temperature, there can be a diffraction when the traversal through the different media or where the temperature gradients exist and this can adversely effect the accuracy of measurements being made. The object of the present invention provides a measuring media path in which the measuring media is of substantially uniform temperature gradient and is free of turbulent flow of air and this is achieved by blowing high pressure air in a direction from the transducer towards the target and, at the same time, measuring the temperature of the high pressure air within a plenum chamber so that an accurate determination or calibration can be made with respect to the speed of sound in the measuring medium or air column between the transducer and the target. As diagrammatically illustrated in FIG. 2A, a fan F blowing on the site will provide some of the advantageous effects disclosed herein. The hot turbulent air around the hot ingot produces a time-varying lensing effect that cuases large fluctuations in echo strength. Blowing air into the region narrows the distribution of the echo amplitudes thus producing a more stable range measurement. Blowing controlled temperature air also improves precision because the speed of sound is estimated more accurately. It will be appreciated that as in the usual electronics processing of the signal, signals well outside the expected range measurements are ignored.

Figure 2B:
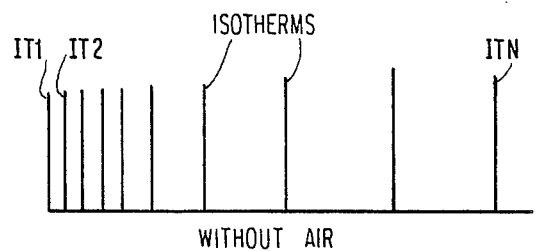
Figure 2C:
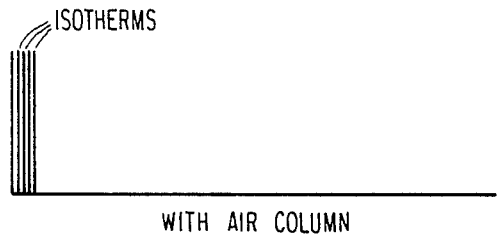
Figure 3:
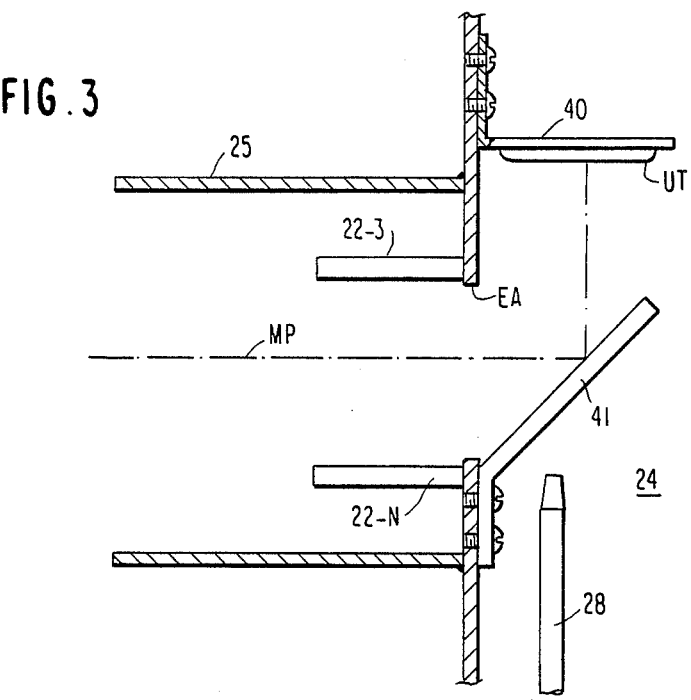
FIG. 3 is a side view illustrating the positioning of the transducer relative to the reflector and the high pressure air jets.
Figure 4:
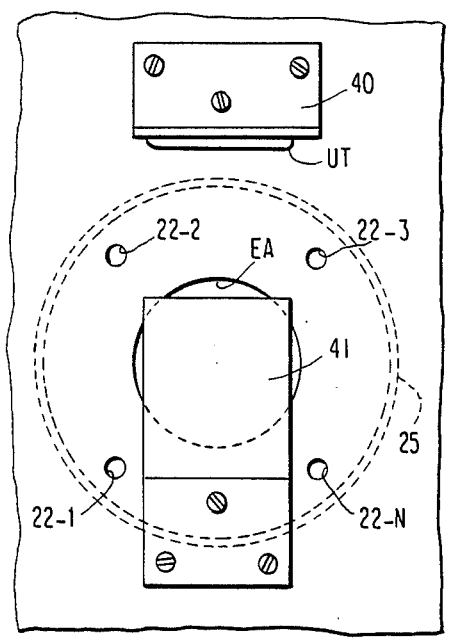
FIG. 4 is the rear or back view of the reflector looking towards the target.
Figure 5:
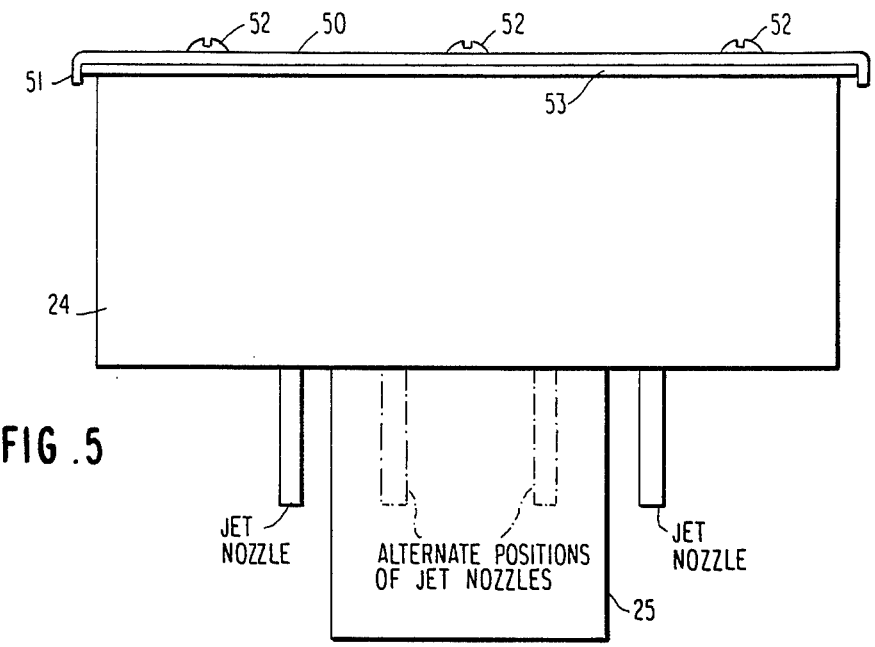
FIG. 5 is a side view of the assembly in its housing.

As indicated in FIG. 2B, the air jets can be located within the cowling 25A (shown in dashed lines in this alternate position). This position may be used where the range is shorter and with a higher frequency of transducer operation.

Figure 6:
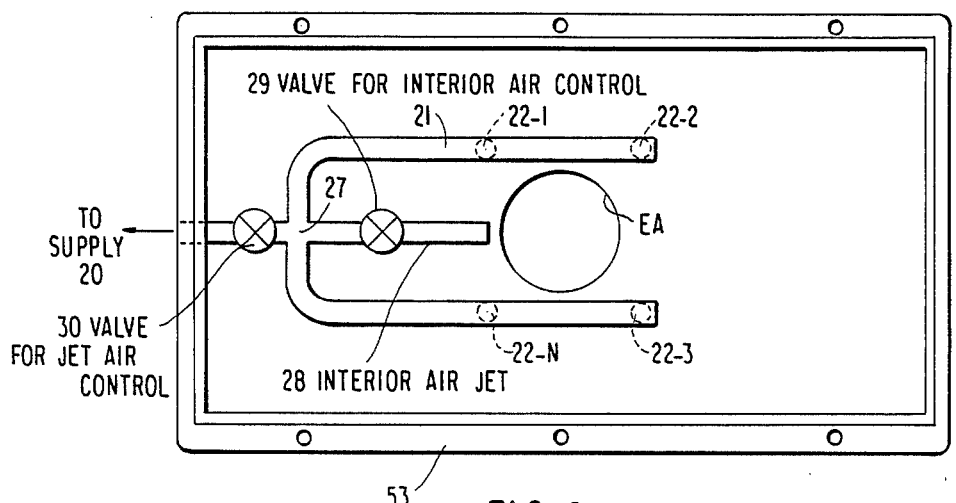
FIG. 6 is a back view of the air supply showing the air manifold and valve location.

The ultrasonic reflector 41 is painted black to prevent reflection of radiant energy from the hot ingot HI to the transducer UT. The exit aperture EA for the ultrasonic energy (see FIG. 6) has a diameter of about 1.7 inches and the stainless-steel cowling 25 has an inside diameter of about 3.5 inches and is about 3.5 inches long.

There are four air jets 22—1, 22—2 . . . 22—N but it will be appreciated that more or less number of jets may be utilized to assure a minimization of turbulence and that the column of air in the measuring path MP is essentially homogeneous in the space between the exit aperture EA and target surface area TA of the hot ingot HI. As noted above, for long ranges of 15-60 inches, the jets are positioned outside the cowl so that the cowl serves as a noise barrier. For shorter range, and a somewhat longer frequency of operation, the jets may be located within the cowling 25. The preferred position is outside the cowling.

The preamp and driver circuitry are mounted behind the bracket 40 supporting the ultrasonic transducer UT. Air jet nozzle 28 supplies the interior of the plenum chamber 24 with air which flows through exit aperture EA, the air supplied by the interior air jet nozzle 28 assures that the temperature of the air inside the plenum chamber is essentially constant and since it flows through exit aperture EA it, forms a part of the column of air between the transducer and the temperature is measured by temperature sensor 31 (which could also be a velocity of sound in air transducer as disclosed in my patent application Ser. No. 149,816, filed Jan. 29, 1988. A cover 50 having a downwardly depending lip 51 is secured by screws 52 to flange 53 forming the plenum chamber 24.

As noted above, a basic feature of this invention lies in the elimination of temperature gradients between the ultrasonic transducer and the hot slab target by flowing air to form an artificial measuring path media comprised of a homogenous column of air impinging on the surface of the hot ingot to be measured to reduce or minimize temperature gradients and reduce or minimize hot turbulent air flow in an area of the surface TA of the hot ingot from which the ultrasonic energy is to be reflected. In the preferred embodiment disclosed herein, the fluid medium under pressure is relatively cool air (at about 150 psi) which is flowed from the ultrasonic transducer to the target to form a temperature homogeneous column of fluid flowing towards and impinging upon the hot target to thereby establish an ultrasonic measuring path to target in which the medium traversing the path of the target is uniform. It is clear that a portion of the measuring path is that portion from the reflector to the transducers. This establishes an artificial measuring path in which the radiant heat eminating from the target is carried away by the flowing column of air so it does not adversely effect range measurement being made by the ultrasonic transducer. Moreover, by mounting the transducer above the reflector, and by causing the reflector to be non-reflective of radiant energy from the hot target but only reflective of ultrasonic energy emanating from the transducer, and by making the measurement of the temperature of air or the velocity of sound in the air at a given temperature inside the plenum chamber greater accuracy in the range measurement is achieved and at reasonable cost.

While there has been shown and described a preferred embodiment of the invention, it will be appreciated that other embodiments and adaptations of the invention will be readily apparent to those skilled in the art and it is intended that such adaptations and obvious modifications as come within the purview of one skilled in the art are intended to be encompassed by the scope of the claims appended hereto.

What is claimed is:

1. In an ultrasonic range measurement system having an ultrasonic transducer for transmitting ultrasonic energy along a measuring path toward a hot target and for receiving reflection echoes of ultrasonic energy from said target, means for measuring the speed of sound in air in said measuring path and electronic means for determining the range to said target from the time of transmission of said ultransonic energy to the receipt of reflection of ultrasonic energy from said target, the improvement comprising, a source of measuring path air under pressure, means for forming a substantially homogenous column of said measuring path air between said ultrasonic transducer and said hot target a plenum chamber, means mounting said ultrasonic transducer within said plenum chamber on an axis at a transverse angle to the axis of said measuring path, and an ultrasonic reflector for reflecting ultrasonic energy from said ultrasonic transducer through an opening in said plenum chamber to said hot target and from said target to said ultrasonic transducer through said opening.

2. The system defined in claim 1, wherein said hot target is a slab which is incandescent and said ultrasonic reflector is substantially non-reflective of radiant energy from said hot target.

3. The system defined in claim 1 including means to introduce air from said source under pressure in said plenum chamber and means for directing air from said plenum chamber to form part of the homogenous air column in said measuring path.

4. The system defined in claim 3 including valve means for controlling air flow in said plenum chamber and in said measuring path.

5. The system defined in claim 3 wherein said means for measuring the speed of sound in said air includes a temperature sensor mounted in said plenum chamber.

6. In an ultrasonic range measurement method in which an ultrasonic transducer transmits ultrasonic energy along an air measuring path toward a hot target which has an ultrasonic measuring area which receives ultrasonic pulse energy and reflects echoes of ultrasonic pulse energy from said ultrasonic measuring area, making an electronic determination of the range to said ultrasonic measuring area on said hot target from the time of transmission of said ultrasonic energy to the receipt of reflection of ultrasonic energy from said ultrasonic measuring area on said hot target and including calibrating said measurement for the speed of sound in the air in said measuring path, the improvement comprising establishing an artificial measuring path of air under pressure to said ultrasonic measuring area by projecting a column of high pressure air between said ultrasonic transducer and said hot target under sufficient pressure to impinge directly upon said ultrasonic measuring area and reduce lensing effects of said hot target on said ultrasonic energy and to enhance the accuracy of range measurements by minimizing the effect of temperature gradients due to the heat radiated from said hot target in said measuring path and narrow the distribution of reflection echo amplitudes to provide a more stable range of measurement and improve precision of range measurement by enhancing the accuracy of speed of sound in the media measurement.

7. An ultrasonic range measurement method in which an ultrasonic transducer transmits ultrasonic energy along a measuring path toward an incandescent steel ingot moving along a path and receives reflection echoes of ultrasonic energy from said incandescent steel ingot, an electronic determination of the range to said incandescent steel ingot from the time of transmission of said ultrasonic energy to the receipt of reflection of ultrasonic energy from said incandescent steel ingot and including calibrating said measurement for the speed of sound in the air in said measuring path, comprising blowing air at a sufficiently high intensity to impinge directly onto an ultrasonic target area of the surface of said incandescent steel ingot to prevent hot turbulent air flow thereover and reduce temperature gradients, and reduce lensing effects on sonic energy adjacent said ultrasonic target area.

8. In a sonic ranging system including transducer means actuatable for transmitting a burst of sonic energy along a measuring path toward a target and for receiving and processing an echo from said target including means for determining the speed of sonic energy in said measuring path so as to produce a time interval related to the range to said target, the improvement comprising means for establishing a flowing column of air flowing from said transducer means to impinge on said target a plenum chamber housing said transducer, an ultrasonic exit aperture formed in said plenum chamber, means mounting said transducer in said plenum chamber and oriented at an angle to the axis of that portion of said measuring path between said exit aperture and said target, and an ultrasonic reflector for directing sonic energy to and from said transducer to said portion of said measuring path.

9. The sonic ranging system defined in claim 8 including means for causing a portion of said column of air to flow through said exit aperture.

10. The sonic ranging system defined in claim 9 including a cowl member coaxial with said portion of said measuring path and aperture and secured to the exterior of said plenum chamber.

11. In a sonic ranging system including transducer means including an exit aperture actuatable for transmitting a burst of sonic energy along a measuring path toward a target and for receiving and processing an echo from said target including means for determining the speed of sonic energy in said measuring path so as to produce a time interval related to the range to said target, the improvement comprising means for establishing a flowing column of air flowing from said transducer means to impinge on said target and wherein said means for establishing a column of air includes a plurality of air nozzles, and means for circumfrentially mounting said plurality of nozzles around said exit aperture.

12. In a sonic ranging system including transducer means actuatable for transmitting a burst of sonic energy along a measuring path toward a target and for receiving and processing an echo from said target including means for determining the speed of sonic energy in said measuring path so as to produce a time interval related to the range to said target, the improvement comprising means for establishing a flowing column of air flowing from said transducer means to impinge on said target and wherein said means for establishing a column of air includes a plurality of nozzles, and a manifold means for supplying said nozzles with air.

13. The sonic ranging system defined in claim 9 wherein said means for causing a portion of said column of air to flow through said exit aperture includes a further nozzle mounted in said plenum chamber and connected to said manifold, and said means for determining the speed of sonic energy in said measuring path includes a temperature sensor mounted in said plenum chamber.

14. The sonic ranging system defined in any of claims 8–13 wherein said target is an object heated to incandescance, and said column of air impinges on said surface of said target at sufficient intensity to minimize the effect of hot turbulent air flow near and around said target.

15. An ultrasonic range measurement method in which an ultrasonic transducer transmits ultrasonic pulse energy along a horizontal path toward an incandescent steel ingot moving along a path and receives reflection echoes of ultrasonic pulse energy from said ingot, an electronic determination of the range to said steel ingot from the time of transmission of said ultrasonic pulse energy to the receipt of reflection of ultrasonic pulse energy from said ingot and including calibrating said measurement for the speed of sound in the air in said measuring path, blowing high pressure air horizontally onto an ultrasonic target area on a side surface of said incandescent steel ingot to prevent hot turbulent air flow over said ultrasonic target area and reduce temperature gradients and the diffraction of sonic energy traveling to and from said incandescent steel ingot in said measuring path.

* * * * *